United States Patent
Patrias (10) Patent No.: US 7,162,307 B2
(45) Date of Patent: Jan. 9, 2007

(54) CHANNEL OCCUPANCY IN MULTI-CHANNEL MEDICAL DEVICE COMMUNICATION

(75) Inventor: Robert A. Patrias, Belle Plaine, MN (US)

(73) Assignee: Medtronic, Inc., Minneapolis, MN (US)

( * ) Notice: Subject to any disclaimer, the term of this patent is extended or adjusted under 35 U.S.C. 154(b) by 616 days.

(21) Appl. No.: 10/364,739

(22) Filed: Feb. 11, 2003

(65) Prior Publication Data

US 2004/0158299 A1   Aug. 12, 2004

(51) Int. Cl.
*A61N 1/08* (2006.01)

(52) U.S. Cl. .................. 607/60; 607/30; 607/31; 128/903

(58) Field of Classification Search ............ 607/30–32, 607/59–60; 128/903–904
See application file for complete search history.

(56) References Cited

U.S. PATENT DOCUMENTS

| 4,287,599 | A |   | 9/1981  | Goncharoff et al. |         |
|-----------|---|---|---------|-------------------|---------|
| 4,893,087 | A |   | 1/1990  | Davis             |         |
| 5,344,431 | A | * | 9/1994  | Merritt et al.    | 607/29  |
| 5,491,469 | A |   | 2/1996  | Schwendeman       |         |
| 5,581,579 | A |   | 12/1996 | Lin et al.        |         |
| 5,674,264 | A | * | 10/1997 | Carter et al.     | 607/57  |
| 6,400,990 | B1|   | 6/2002  | Silvian           | 607/60  |
| 6,470,215 | B1|   | 10/2002 | Kraus et al.      | 607/60  |
| 6,643,541 | B1| * | 11/2003 | Mok et al.        | 600/546 |
| 6,801,807 | B1| * | 10/2004 | Abrahamson        | 607/60  |
| 2001/0049544 | A1 |  | 12/2001 | Lee            | 607/59  |

FOREIGN PATENT DOCUMENTS

CA     2238984     6/1997

\* cited by examiner

*Primary Examiner*—Robert Pezzuto
*Assistant Examiner*—Shevon Johnson
(74) *Attorney, Agent, or Firm*—Paul H. McDowall; Girma Wolde-Michael (57) ABSTRACT

In general, channel occupancy techniques for multi-channel medical device communication are provided. More specifically, techniques are described for maintaining a communication session between an external device and an implantable medical device (IMD) to reduce the potential for conflict with other programmers. A device, such as an external device, includes a transmit module to transmit telemetry signals to an implantable medical device over a communication channel, and a control unit that communicates data to the IMD via the transmit module. The control unit communicates idle messages over the communication channel during gaps within the data communication to the IMD.

28 Claims, 4 Drawing Sheets

CHANNEL OCCUPANCY IN MULTI-CHANNEL MEDICAL DEVICE COMMUNICATION

TECHNICAL FIELD

The invention relates generally to medical devices and, more particularly, to techniques for communicating with medical devices.

BACKGROUND

Implantable medical devices (IMD) are commonly used to treat and monitor patients. Examples of an IMD include implantable cardiac pacemakers, implantable defibrillators, implantable pacemaker/cardioverter/defibrillators, implantable muscular stimulus devices, implantable brain stimulators, other implantable organ stimulation devices, implantable drug delivery devices, implantable monitors, and the like. These disparate medical devices often apply one or more medical treatments, and generate a wealth of physiological data relating to the condition of the patient.

This physiological data is often collected by use of telemetry, which generally refers to communication of data, instructions, and the like between an IMD and an external device, such as a medical device programmer or an external monitor. A communication "session" is established to communicate the physiological data to the external device, and to communicate any controls or commands from the external device to the IMD. In this manner, the external device may obtain diagnostic data, event marker data, activity data and other data collected or identified by the IMD. The physiological data may be used to program the IMD for delivery of new or modified therapies. As a result, telemetry between an IMD and the external device can be used to improve or enhance therapy.

To establish the communication session, the external device often examines a defined frequency spectrum to select one of a number of defined communication channels. During this process, the medical device programmer examines the channels individually in an attempt to select an open channel. If the external device detects activity on the channel, e.g., communication between another device and an IMD, the external device examines a different channel.

Once an external device and an IMD have established a communication session, the external device and the IMD communicate in a bi-directional fashion using downlink and uplink communication messages. The external device and the IMD alternate between downlink and uplink communication messages, respectively. In particular, the external device transmits downlink communication messages and receives uplink communication messages. The IMD receives downlink communication messages and transmits uplink communication messages. Each downlink and uplink message pair may form a single frame within the communication session.

During the communication session, the data exchange between the devices may vary greatly depending on a number of factors, including the amount of physiological data and programming commands to be transferred. For example, the external device and IMD may exchange uplink and downlink messages at a reduced rate when higher-rates are unnecessary, thereby reducing power consumption by the IMD. In other words, when there is less information to transmit from the IMD to the external device, the IMD transmits fewer uplink messages. This reduced transmission allows the implant to save energy associated with the transmit operations. Similarly, the external device transmits fewer downlink messages when there is less information to downlink to the IMD. This allows the IMD to save energy associated with the receive operation.

These reduced transmissions may cause significant communication gaps in the communication session, i.e., periods during which there is no communication between the devices. For example, a communication gap may occur when the IMD is collecting physiological data in real-time per the request of the external device. During these gaps, another external device may erroneously determine that the communication channel is unused, and may attempt to initiate a communication session. This usage may interfere with the previously established communication session, and may result in data loss, consumption of additional power by the IMD in attempting to respond to erroneous communications, and possibly premature termination of the original communication sessions.

SUMMARY

In general, the invention is directed to channel occupancy techniques for multi-channel medical device communication. More specifically, techniques are described for maintaining a communication session between an external device, e.g., a medical device programmer or a monitor, and an implantable medical device (IMD) to reduce the potential for conflict with other programmers. For exemplary purposes, the techniques are described in reference to a medical device programmer. Nevertheless, the techniques may be applicable to any form of multi-channel communication between an external device and an IMD.

During the communication session, the medical device programmer and the IMD may vary the rate at which data is exchanged via the communication channel depending on the amount of information to uplink or downlink, thereby conserving IMD power associated with the receive and transmit operations.

During periods when the IMD is not listening, i.e., has disabled the receive operation, the programmer may transmit additional downlink idle messages in the form of idle packets to occupy the communication channel when the channel would otherwise be unused. Moreover, the programmer may dynamically adjust the transfer rate of the idle packets to offset the reduced data exchange rate between the programmer and the IMD. In other words, the programmer may automatically insert an increased amount of idle packets as the IMD and the programmer agree to transfer less data, i.e., consume less uplink and downlink messages. Similarly, the programmer may automatically insert fewer idle packets in response to increased uplink and downlink data transfer rates.

In one embodiment, the invention is directed/to a method comprising communicating data from a medical device programmer to an implantable medical device using a communication channel, and transmitting idle messages from the medical device programmer via the communication channel during gaps within the data communication.

In another embodiment, the invention is directed to a method comprising transmitting downlink communications from a medical device programmer to an implantable medical device at a first rate, wherein the downlink communications include data and idle messages. The method further comprises receiving the downlink communications with the implantable medical device at a second rate slower than the first rate to receive the data packets and not the idle messages.

In another embodiment, the invention is directed to a device comprising a transmit module to transmit telemetry signals to an implantable medical device over a communication channel, and a control unit that communicates data to the implantable medical device via the transmit module, and communicates idle messages over the communication channel during gaps within the data communication to the implantable medical device.

In another embodiment, the invention is directed to system comprising a medical device programmer to transmit downlink communications including data and idle messages through a communication channel at a first rate, and an implantable medical device to receive the downlink communications at a second rate slower than the first rate to receive the data packets and not the idle messages.

In another embodiment, the invention is directed to a computer-readable medium containing instructions. The instructions cause a programmable processor to communicate data from a medical device programmer to an implantable medical device using a communication channel, and transmit idle messages from the medical device programmer via the communication channel during gaps within the data communication.

In another embodiment, the invention is directed to a programmer comprising means for transmitting telemetry signals to an implantable medical device over a communication channel, and means for communicates data to the implantable medical device via the telemetry signals, wherein the communication means communicates idle messages over the communication channel during gaps within the data communication.

This invention may provide one or more advantages. For example, the programmer may be able to achieve increased channel occupancy. This increased channel occupancy may assist other medical device programmers in correctly assessing the usage of the communication channel. Moreover, because the IMD is configured to disregard, i.e., not receive, the downlink messages while the programmer transmits the idle packets, the IMD does not consume additional energy even though channel communication has been increased.

The details of one or more embodiments of the invention are set forth in the accompanying drawings and the description below. Other features, aspects and inventive elements of the invention will be apparent from the description and drawings, and from the claims.

DETAILED DESCRIPTION

Figure 1:
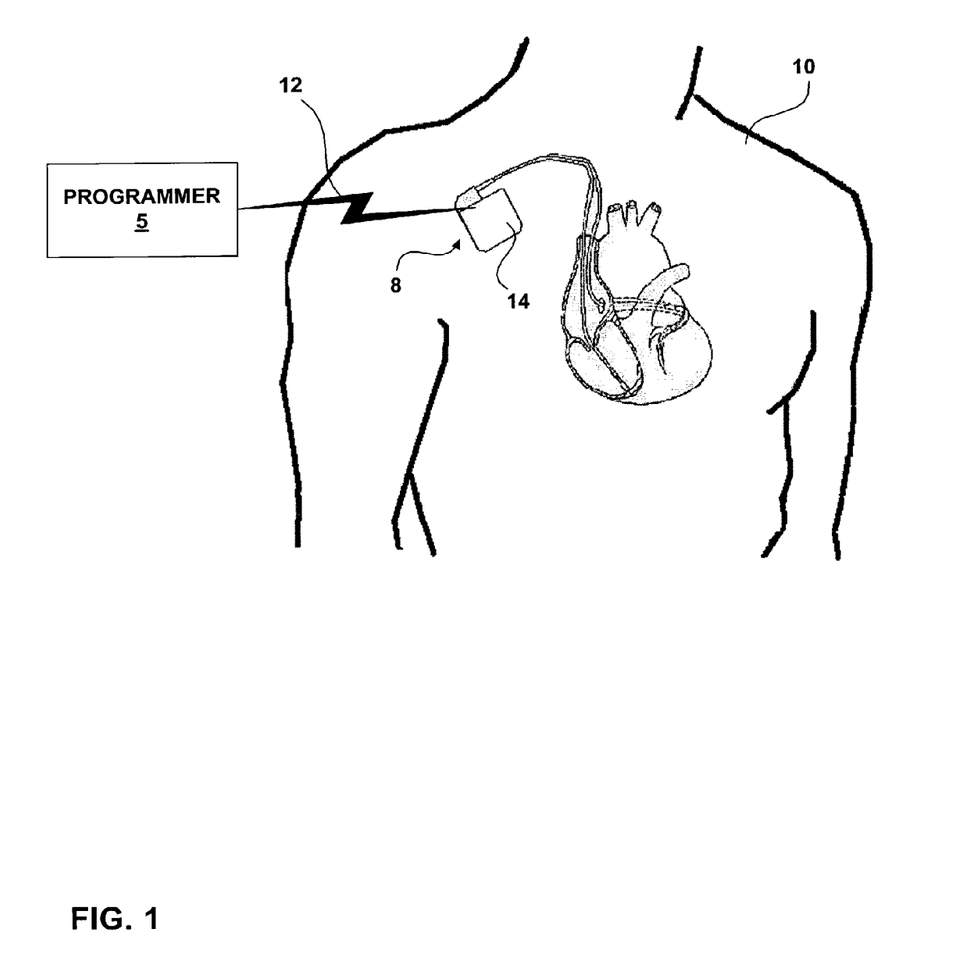
FIG. 1 is a conceptual diagram illustrating a programmer in communication with an exemplary implantable medical device ("IMD") implanted in a patient.

FIG. 1 is a conceptual diagram illustrating a programmer 5 in communication with an exemplary implantable medical device ("IMD") 8 implanted in a patient 10. For exemplary purposes, IMD 8 is illustrated as an implantable cardiac pacemaker that delivers pacing pulses to a heart of patient 10. IMD 8 includes a hermetically-sealed enclosure 14 that may contain various elements. By way of example, enclosure 14 may house an electrochemical cell, e.g., a lithium battery, circuitry that controls device operations such as delivery of stimulation pulses and records sensed events, physiological activity and patient conditions, and a control unit coupled to an antenna to communicate with programmer 5 via wireless telemetry signals 12.

Programmer 5 uses telemetry signals 12 to initiate a communication "session" with IMD 8. During the session, programmer 5 may program IMD 8 to deliver particular therapies to patient 10, and may interrogate IMD 8 to obtain "session" data. The session data may include, for example, physiological data, e.g., diagnostic data, event marker data, activity data and other data currently stored by IMD 8. In this manner, telemetry allows bi-directional communication between IMD 8 and programmer 5.

Programmer 5 and IMD 8 communicate via telemetry in accordance with one or more wireless communication techniques, such as standard RF telemetry protocols. Programmer 5 and IMD 8 may use, for example, electromagnetic signals, such as radio frequency (RF) signals and infrared (IR) frequency signals, sound waves, or even the patient's flesh as the transmission medium. For example, conventional RF telemetry communication protocols for communicating with IMDs may be employed to effect communications between IMD 8 and programmer 5.

Although illustrated as an implantable cardiac pacemaker, IMD 8 may take the form of a variety of other implantable medical devices. Another example of an implantable medical device is a pacemaker-cardioverter-defibrillator ("PCD"). Other examples include an implantable brain stimulator, an implantable gastric system stimulator, an implantable nerve stimulator or muscle stimulator, an implantable lower colon stimulator (e.g., in graciloplasty applications), an implantable drug or beneficial agent dispenser or pump, an implantable cardiac signal loop or other type of recorder or monitor, an implantable gene therapy delivery device, an implantable incontinence prevention or monitoring device, an implantable insulin pump or monitoring device, and so on. Thus, programmer 5 may receive a wide variety of session data including heart rate, heart rate variability, blood glucose levels, oxygen saturation, partial pressure of oxygen in the blood, blood pressure, baro-reflex measures, electrogram morphologies, lung wetness, and the like.

Although illustrated by way of example with respect to an IMD, the techniques described herein are not so limited, and may be applied to non-implanted medical devices configured for interrogation and programming by a programmer 5. As a non-implanted medical device, IMD 8 may comprise a variety of patient monitoring devices, such as an external blood pressure monitor, an external heart rate monitor that measures heart rate and heart rate variability, an external blood glucose monitor, a user input device for generating an electronic questionnaire regarding patient systems or status, a Holter monitor, an external EKG or ECG monitor, an external cardiac signal loop recorder, a temporary cardiac pacing system having an external pulse generator, and the like. In addition, programmer 5 may communicate with external drug delivery systems that may provide physiological data in the form of recent dosage levels, dosing history, and the like. Another example is an external device for testing the blood to provide a variety of information, such as prothrombin time, which may assist in titrating anti-coagulation medication or the current levels of B-type natriuretic peptide (BNP), and aid the diagnosis and management of congestive heart failure (CHF).

Moreover, in some cases, IMD 8 may correspond to a medical device used on non-human mammals or other animals. In short, the techniques described herein may be readily used with a wide variety of medical devices including implanted and non-implanted medical devices used to deliver therapy or gather physiological information in humans, mammals, or other types of living beings.

To establish a communication session with IMD 8, programmer 5 examines a frequency spectrum to select one of a number of defined communication channels. During this process, programmer 5 may examine the channels individually in an attempt to select an unoccupied channel. Upon detecting an unoccupied channel, programmer 5 attempts to initiate the communication session with IMD 8. Once established, programmer 5 and IMD 8 communicate in bi-directional fashion using downlink and uplink communication messages. In one embodiment, programmer 5 and IMD 8 communicate using a frame-based protocol in which each downlink and uplink message pair may form a single frame.

During the communication session, programmer 5 and IMD 8 may vary the rate at which data is exchanged via the communication channel depending on the amount of information to uplink or downlink. For example, IMD 8 may transmit fewer uplink messages, i.e., skip uplink messages for certain frames, when there is less information to transmit. In this manner, IMD 8 may conserve power associated with the transmit operation. In similar fashion, IMD 8 listens for downlink messages from programmer 5 at the reduced rate, thereby conserving power associated with the receive operation.

During periods when IMD 8 is not listening, programmer 5 transmits downlink idle messages, which may be in the form of idle packets, to occupy the communication channel when the channel would otherwise be unused. Moreover, programmer 5 may dynamically adjust the transfer rate of the idle packets to offset the reduced data exchange rate between the programmer and IMD 8. In other words, programmer 5 may automatically insert more idle packets as IMD 8 and the programmer agree to transfer less data, i.e., consume less uplink and downlink messages. Similarly, programmer 5 may automatically insert fewer idle packets in response to increased uplink and downlink data transfer rates.

In this manner, programmer 5 can achieve increased channel occupancy, and may maintain at least a threshold occupancy rate for the channel. For example, programmer 5 utilize idle packets to achieve at substantially meet or exceed a configurable threshold occupancy, e.g., 25%, 50% occupancy, 75% occupancy, 90% occupancy, or more. This increased channel occupancy may assist other medical device programmers that might otherwise incorrectly assess the usage of the communication channel. As IMD 8 is configured to not receive downlink messages during the transmission of the idle packets, IMD 8 does not consume additional energy as a result of the increased downlink communications. Yet, programmer 5 keeps the channel intact so that two-way communication can be maintained at the reduced rate.

For exemplary purposes, the techniques are described herein in reference to a medical device programmer, e.g., programmer 5. Nevertheless, the techniques may be applicable to any form of multi-channel communication between an external device and an IMD.

Figure 2:
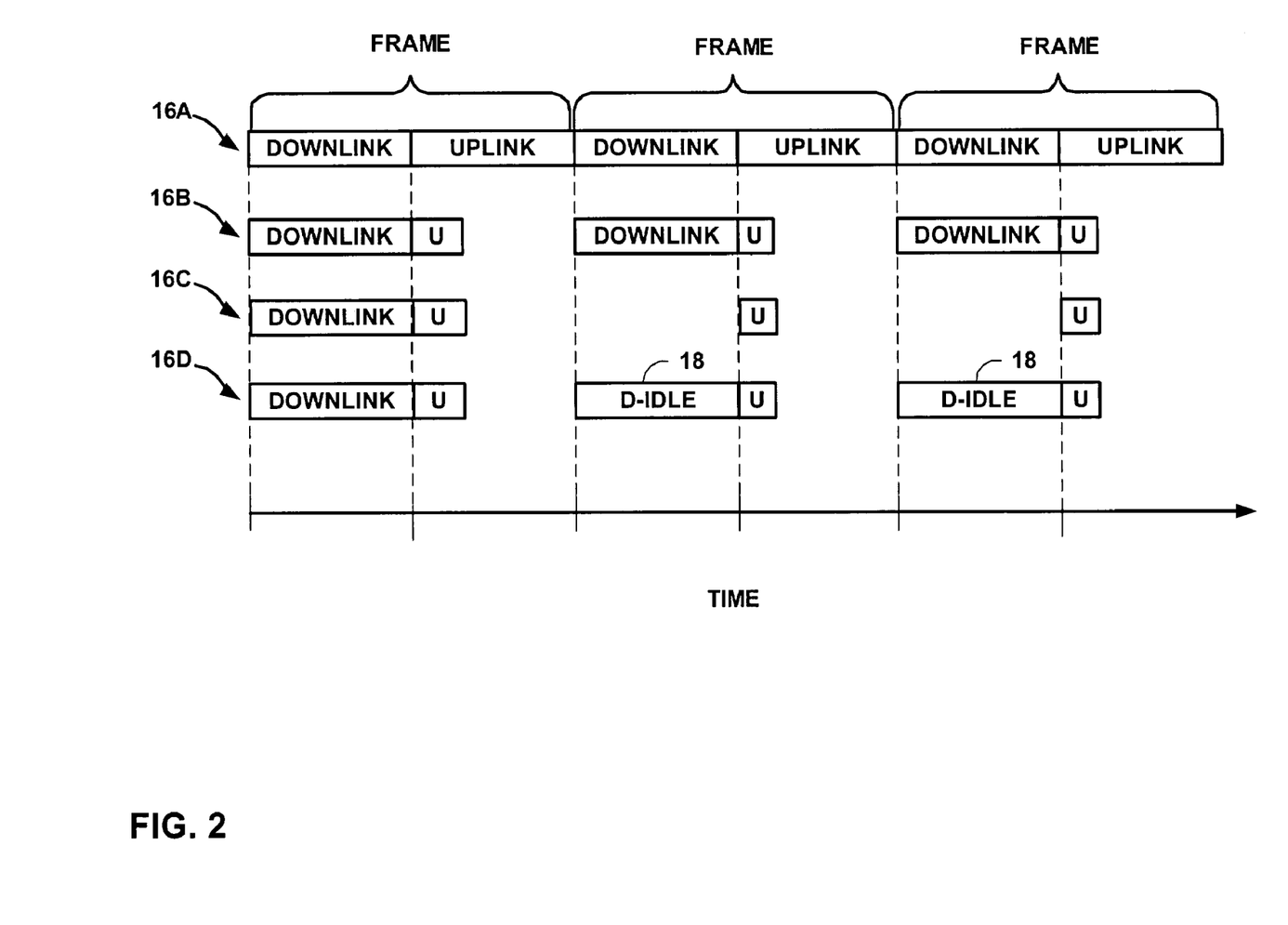
FIG. 2 is a timing diagram that illustrates channel occupancy techniques.

FIG. 2 is a timing diagram that further illustrates the channel occupancy techniques described herein. In particular, FIG. 2 illustrates four channel communication modes 16A–16D for communicating between a medical device programmer and an IMD.

Mode 16A illustrates normal communication between a programmer 5 and an IMD 8 in which each frame includes a downlink message and an uplink message. In other words, mode 16A illustrates complete utilization of the communication channel without a reduction in the rate of data exchange. Mode 16B illustrates a reduction in uplink messages, while mode 16C illustrates a reduction in uplink and downlink messages. Modes 16A–16C may, for example, be employed by conventional programmers and IMDs.

In contrast, mode 16D illustrates the transmission of idle packets (D-IDLE) 18 by programmer 5 to achieve higher channel occupancy without requiring increase power consumption by IMD 8, as described above. As illustrated, programmer 5 (FIG. 1) inserts idle packets 18 within the unused downlink portions of frames, thereby reducing communication gaps within the channel. Programmer 5 may transmit idle packets 18 as a conventional downlink message, but may include data identifying the packets as idle and, therefore, not requiring any response. During these periods, IMD 8 suspends receive and transmit operation, thereby automatically disregarding idle packets 18 and conserving power.

Figure 3:
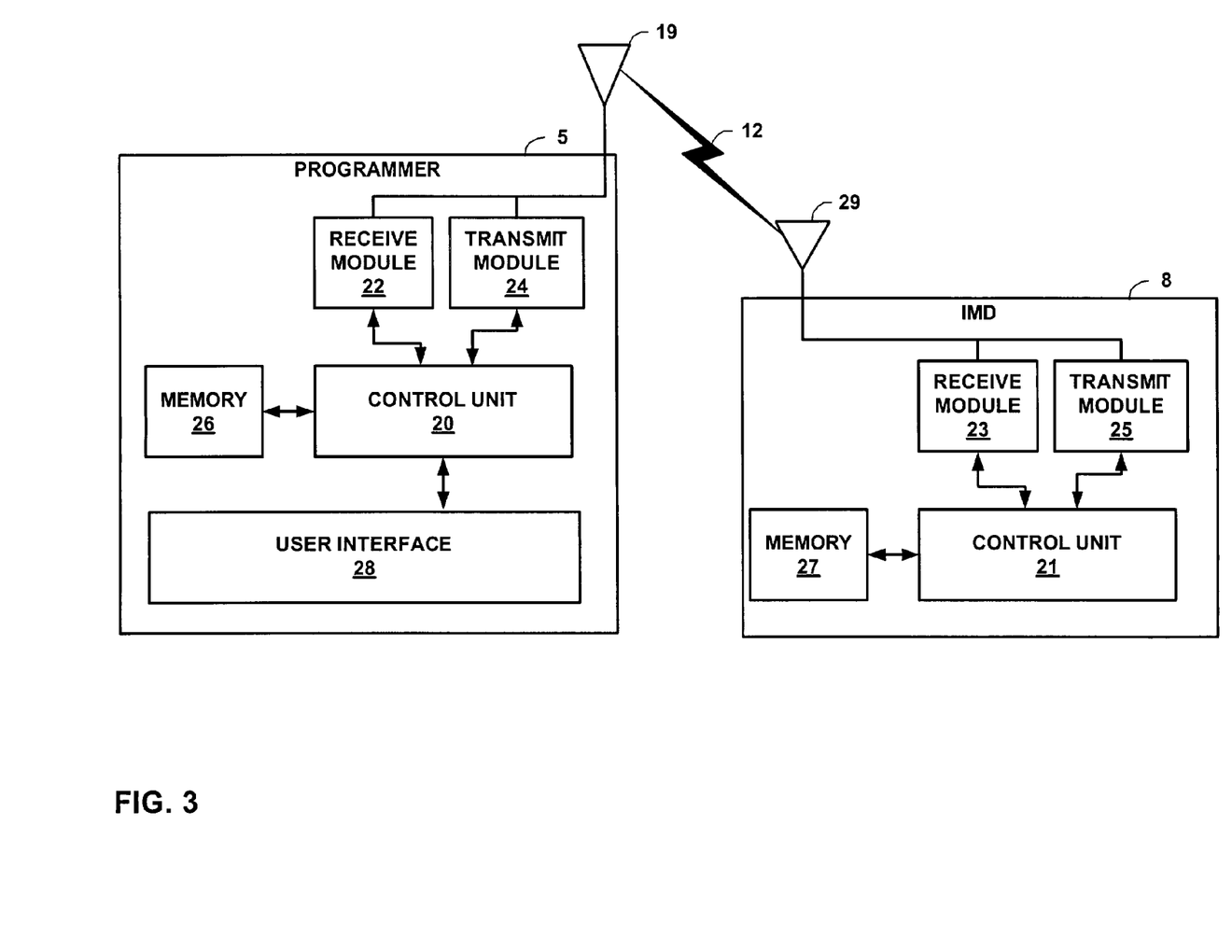
FIG. 3 is an exemplary block diagram of a programmer and an IMD that achieve increased channel occupancy as described herein.

FIG. 3 is an exemplary block diagram of a programmer 5 and an IMD 8 that achieve increased channel occupancy as described herein. As illustrated, programmer 5 may include an antenna 19, a control unit 20, a receive module 22, a transmit module 24, a memory 26, and a user interface 28. Antenna 19 may send and receive electromagnetic telemetry signals 12, such as radio frequency signals, as directed by control unit 20. The invention, however, is not limited for use with electromagnetic telemetry signals, but may also used with other telemetry signals, including sound waves.

In operation, control unit 20 of programmer 5 receives telemetry signals via receive module 22 and antenna 19. Antenna 19 may be tuned to a frequency band that covers the defined channels for communicating with IMD 8. Upon receiving a signal, receive module 22 conditions the signals so that control unit 20 may accurately process the signal. For example, receive module 22 may include an analog-to-digital converter (ADC) to digitize the received signal for processing by control unit 20. Receive module 22 may also include one or more amplifiers, a variable gain amplifier (VGA), one or more filters, automatic gain control (AGC), if needed, and a phase-locked loop for synchronizing a received signal so that an in-phase sample can be identified. These and other components of receive module 22 condition the received telemetry signal as required by control unit 22 so that signal analysis can be performed.

Transmit module 24 conditions output signals for wireless transmission to IMD 8 via antenna 19. For example, control unit 20 may generate timed output signals in order to communicate with the respective medical device 8 via telemetry. Transmit module 24 receives the output signals from control unit 20, and amplifies, modulates, or otherwise processes the signals for transmission via antenna 19. For example, transmit module 24 may include transmit circuitry for driving antenna 19, such as a set of field effect transistors (FET) that output relatively large output voltage pulses in response to relatively small input voltages received from control unit 20. Transmit module 24 may also include various other filters, amplifiers, or the like, that may be selectively activated based on the given communication mode.

As described, control unit 20 outputs signals via transmit module 24 to establish a communication session with IMD 8. During the communication session, control unit 20 directs receive module 22 and transmit module 24 to exchange data with IMD 8 at a variable rate depending on the amount of information to uplink or downlink. Moreover, control unit 20 directs transmit module 24 to transmit downlink communication messages in the form of idle packets 18 to occupy the communication channel when the channel would otherwise be unused. Moreover, control unit 20 may dynamically adjust the transfer rate of the idle packets 18 to offset the reduced data exchange rate between the programmer and IMD 8. In this manner, control unit 20 can achieve increased channel occupancy, which may assist other medical device programmers in correctly assessing the usage of the communication channel.

Control unit 20 operates according to executable instructions fetched from one or more computer-readable media, e.g., memory 26. Examples of such media include random access memory (RAM), read-only memory (ROM), non-volatile random access memory (NVRAM), electrically erasable programmable read-only memory (EEPROM), flash memory, and the like.

The functions of control unit 20 may be implemented by executing the instructions of the computer-readable medium with one or more processors, discrete hardware circuitry, firmware, software executing on a programmable processor, or a combination of any of the above. For example, control unit 20 may include a programmable digital signal processor (DSP). Examples of DSPs include the TI-TMS320C2000 family of DSPs, such as the model number TI-TMS320LC2406 DSP, commercially available from Texas Instruments Incorporated of Dallas Tex., USA. Other DSPs and programmable microprocessors, however, could be used.

In similar fashion, IMD 8 may include an antenna 29, a control unit 21, a receive module 23, a transmit module 25, and a memory 27. Antenna 29 sends and receives electromagnetic telemetry signals 12 for communication with programmer 5. Receive module 23 conditions received signals so that control unit 20 may accurately process the signal. Transmit module 25 conditions output signals for wireless transmission to programmer 5 via antenna 29. Control unit 21 outputs signals via receive module 23 and transmit module 25 to establish a communication session with programmer 5, and exchange data with the programmer at a variable rate depending on the amount of information to uplink or downlink. Control unit 21 operates according to executable instructions fetched from one or more computer-readable media, e.g., memory 27. Examples of such media include random access memory (RAM), read-only memory (ROM), non-volatile random access memory (NVRAM), electrically erasable programmable read-only memory (EEPROM), flash memory, and the like.

Figure 4:
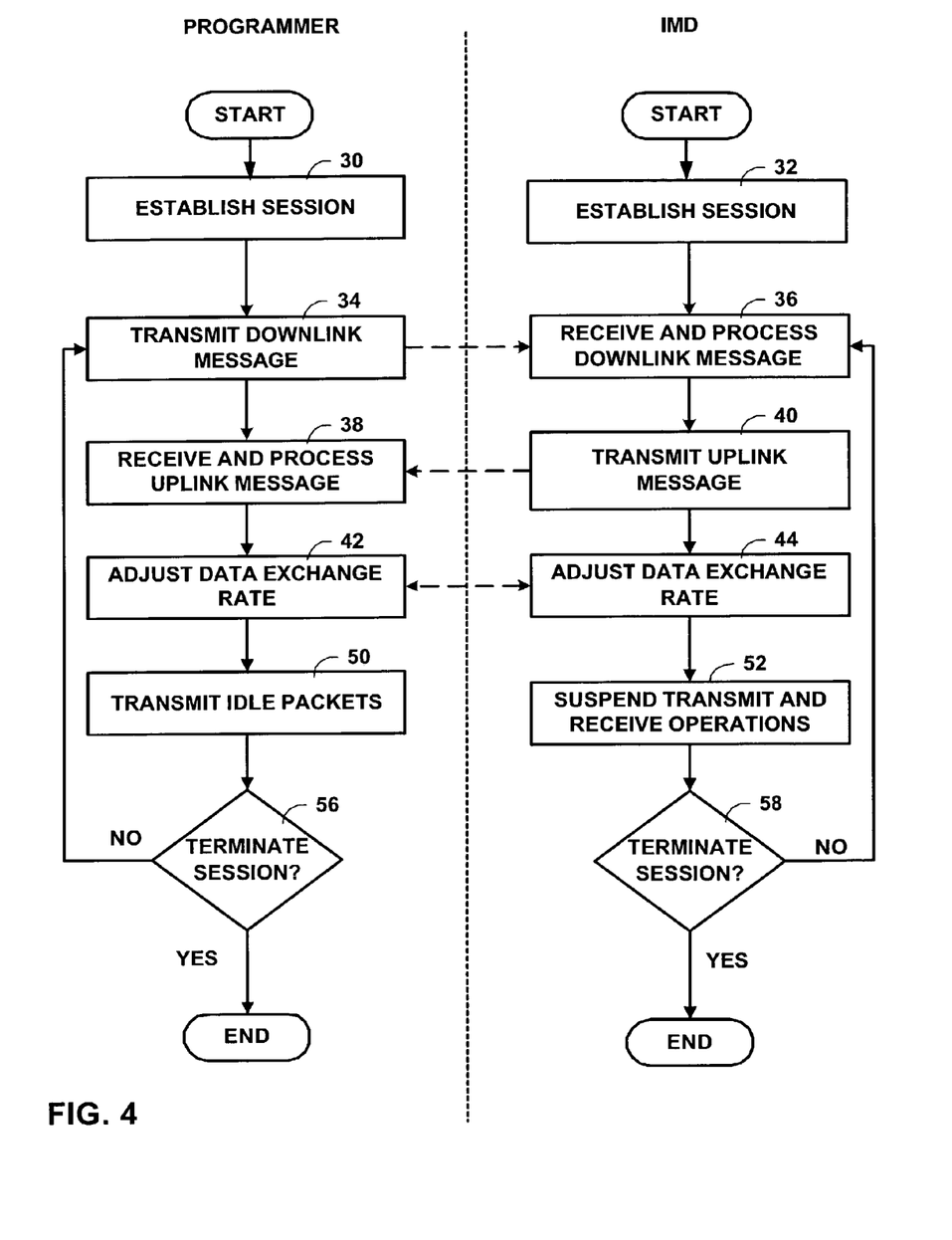
FIG. 4 is a flowchart illustrating example operation of a programmer and an IMD implementing channel occupancy techniques.

FIG. 4 is a flowchart illustrating example operation of programmer 5 and IMD 8 in accordance with the channel occupancy techniques described herein. Initially, programmer 5 and IMD 8 establish a telemetry communication session over a communication channel (30, 32).

As described above, programmer 5 and IMD 8 may communicate using a frame-based protocol in which each frame has a downlink communication and an uplink communication. In particular, programmer 5 transmits a downlink communication to IMD 8 (34), which receives and processes the communication (36). In response, IMD 8 may transmit an uplink message (40), which programmer 5 receives and processes (38).

During this process, programmer 5 and IMD 8 may agree to adjust a data exchange rate for the communication channel (42, 44). For example, programmer 5 and IMD 8 may agree to reduce the uplink and downlink messages of the frames, and may even agree to skip certain messages or entire frames altogether. In response, programmer 5 transmits idle packets 18 within the communication channel (50) during periods when IMD 8 has suspended operation (52). Programmer 5 adjusts the rate of transmitting the idle packets 18, i.e., the number of frames in which idle packets 18 are transmitted, to accommodate for the reduction in the data exchange rate between the programmer and IMD 8. As a result, programmer 5 may transmit downlink communications, including data and idle packets 18, at a rate greater than the receive rate of IMD 8. By coordinating the rates, programmer 8 transmits the idle packets 18 during periods when IMD 8 has suspended operations, and is not receiving the downlink communications. This process continues until the session is terminated (56, 58).

Various embodiments of the invention have been described. These and other embodiments are within the scope of the following claims.

What is claimed is:

1. A method for maintaining a communication session between an external programmer device and an implantable medical device (IMD) to reduce the potential for conflict with other external programmer devices, comprising:
    communicating data from a first external IMD programmer device to an IMD via a communication channel controlled by a control unit; and transmitting idle messages from the external device via the communication channel during gaps within the data communication to reduce the potential for conflict with one or more other external IMD programmer devices
    establishing a communication session accordance with a frame-based protocol in which each frame has a downlink communication and an uplink communication to communication the data from the external device to the implantable medical device;
    communicating the idle messages during the downlink communications of the frames;
    transmitting the downlink communications of the frames with the medical device at a first rate; and
    receiving the downlink communications with the implantable medical device at a second rate slower than the first rate to receive only the downlink communications carrying data and not the idle messages.

2. The method of claim 1, wherein transmitting idle messages comprises transmitting the idle messages at a transmit rate to maintain at least a threshold occupancy rate for the communication channel.

3. The method of claim 1, wherein threshold occupancy rate exceeds at least about 50% occupancy of the communication channel.

4. The method of claim 1, wherein threshold occupancy rate exceeds at least 90% occupancy of the communication channel.

5. The method of claim 1, wherein transmitting idle messages comprises transmitting the idle messages when the implantable medical device is not receiving messages from the communication channel.

6. The method of claim 1, further comprising:
    adjusting a rate for communicating the data via the communication channel; and adjusting a rate for transmitting the idle messages in response to the adjustment to the data communication rate.

7. The method of claim 1, further comprising:
adjusting the first rate; and
adjusting the second rate in response to the adjustment of the first rate to maintain at least a threshold occupancy of the communication channel.

8. The method of claim 7, wherein adjusting the first and adjusting the second rate comprises decreasing the first rate and increasing the second rate.

9. A method for maintaining a communication session between an external programmer device and an implantable medical device (IMD) to reduce the potential for conflict with other external programmer devices, comprising:
transmitting downlink communications from a first external programming device to an implantable medical device (IMD) at a first rate, wherein the downlink communications include data messages and idle messages; and
receiving the downlink communications with the (IMD) at a second rate slower than the first rate to receive the data messages and not the idle messages to reduce the potential for communication conflict between the first external programming device, the IMD, and other programming devices.

10. The method of claim 9, further comprising:
reducing the first rate to reduce power consumed by the implantable medical device; and
increasing the second rate in response to the reduction of the first rate to maintain at least a threshold occupancy of the communication channel.

11. The method of claim 9, further comprising setting the first and second rates to transmit the idle messages from the external device during periods when the implantable medical device is not receiving the downlink communications.

12. The method of claim 9, wherein the external device comprises one of an external medical device programmer and an external monitor.

13. A device adapted for maintaining a communication session between an external programmer device and an implantable medical device (IMD) to reduce the potential for conflict with other external programmer devices, comprising:
a transmit module to transmit telemetry signals to an IMD over a communication channel; and
a control unit adapted to communicate data to the IMD via the transmit module, and to communicate idle messages via the transmit module over the communication channel during gaps within the data communication to the IMD,
wherein the control unit establishes a communication session in accordance with a frame-based protocol in which each frame has a downlink communication and an uplink communication to communicate the data to the implantible medical device, and communicates the idle messages during the downlink communications of the frames,
wherein the control unit outputs the downlink communications of the frames to include the idle messages and the data at a transmit rate that exceeds a receive rate of the implantable medical device.

14. The device of claim 13, wherein the control unit communicates the idle messages at a communication rate selected to maintain at least a threshold occupancy rate for the communication channel.

15. The device of claim 14, wherein threshold occupancy rate exceeds at least 50% occupancy of the communication channel.

16. The device of claim 14, wherein threshold occupancy rate exceeds at least 90% occupancy of the communication channel.

17. The device of claim 13, wherein the control unit communicates the idle messages when the implantable medical device is not receiving messages from the communication channel.

18. The device of claim 13, wherein the control unit adjusts a rate for communicating the data via the communication channel, and adjusts a rate for transmitting the idle messages in response to the adjustment to the data communication rate.

19. The device of claim 13, wherein the device comprises one of an external medical device programmer and an external monitor.

20. A system comprising:
an external device to transmit downlink communications including data messages and idle messages through a communication channel at a first rate; and
an implantable medical device to receive the downlink communications at a second rate slower than the first rate to receive the data messages and not the idle messages.

21. The system of claim 20, wherein the external device reduces the first rate to reduce power consumed by the implantable medical device, and increases the second rate in response to the reduction of the first rate to maintain at least a threshold occupancy of the communication channel.

22. The system of claim 21, wherein threshold occupancy rate exceeds at least 50% occupancy of the communication channel.

23. The system of claim 21, wherein threshold occupancy rate exceeds at least 90% occupancy of the communication channel.

24. The system of claim 20, wherein the external device and the implantable medical device set the first and second rates to transmit the idle messages from the external device during periods when the implantable medical device is not receiving the downlink communications.

25. The system of claim 20, wherein the external device comprises one of an external medical device programmer and an external monitor.

26. A computer-readable medium comprising instructions for causing a programmable processor to maintain a communication sessions between a first external programmer device and an implantable medical device (IMD) to reduce the potential for conflict with other external programmer devices, comprising:
executable instructions for communicating data from an external device to an implantable medical device (IMD) using a wireless communication channel; and
executable instructions for transmitting idle messages from the external devices to the IMD via the communication channel during gaps within the data communication to reduce the potential for conflict with one more other external programmer devices;
executable instruction for establishing a communication session in according with a frame-based protocol in which each frame has a downlink communication and an uplink communication to communicate the data from the external device to the IMD;

executable instructions for communicating the idle messages during the downlink communication of the frames;

executable instructions for transmitting the downlink communications of the frames with the IMD at a first rate; and executable instructions for receiving the downlink communications by the IMD at a second rate slower than the first rate to receive only the downlink communications carrying data and not the idle messages.

27. The computer-readable medium of claim 26, further comprising executable instructions to cause the processor to transmit the idle messages at a transmit rate to maintain at least a threshold occupancy rate for the communication channel.

28. The computer-readable medium of claim 26, further comprising:

executable instructions to cause the processor to transmit the idle messages when the IMD is not receiving messages from the communication channel.

* * * * *

UNITED STATES PATENT AND TRADEMARK OFFICE
CERTIFICATE OF CORRECTION

PATENT NO. : 7,162,307 B2  Page 1 of 1
APPLICATION NO. : 10/364739
DATED : January 9, 2007
INVENTOR(S) : Patrias

It is certified that error appears in the above-identified patent and that said Letters Patent is hereby corrected as shown below:

Column 8, line 38 please change "session accordance" to --session in accordance--.

Column 8, line 41 please change "to communication the" to --to communicate the--.

Signed and Sealed this

Second Day of October, 2007

JON W. DUDAS
*Director of the United States Patent and Trademark Office*